(12) United States Patent
Aikawa

(10) Patent No.: US 9,632,453 B2
(45) Date of Patent: Apr. 25, 2017

(54) DIFFERENTIAL TRANSFORMER MAGNETIC PERMEABILITY SENSOR

(71) Applicant: KYOCERA Document Solutions Inc., Osaka (JP)

(72) Inventor: Yukihiro Aikawa, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 89 days.

(21) Appl. No.: 14/669,543

(22) Filed: Mar. 26, 2015

(65) Prior Publication Data

US 2015/0277280 A1    Oct. 1, 2015

(30) Foreign Application Priority Data

Mar. 31, 2014  (JP) .................................. 2014-071663

(51) Int. Cl.
  *G03G 15/08* (2006.01)
  *G01R 33/028* (2006.01)
  (Continued)

(52) U.S. Cl.
  CPC ......... *G03G 15/0829* (2013.01); *G01N 27/72* (2013.01); *G01R 33/028* (2013.01);
  (Continued)

(58) Field of Classification Search
  CPC .... G03G 15/08; G03G 15/028; G01R 33/028; G01R 33/04
  (Continued)

(56) References Cited

U.S. PATENT DOCUMENTS 6,429,651 B1 * 8/2002 Choi ...................... G01R 33/04
                                                    324/249
8,994,367 B2    3/2015 Aikawa
(Continued)

FOREIGN PATENT DOCUMENTS

EP         2584368 A2    4/2013
JP     2000-131406 A     5/2000
(Continued)

OTHER PUBLICATIONS

The extended European search report issued by the European Patent Office on Aug. 17, 2015, which corresponds to European Patent Application No. 15160801.5-1560 and is related to U.S. Appl. No. 14/669,543.

(Continued)

*Primary Examiner* — Arleen M Vazquez
*Assistant Examiner* — Neel Shah
(74) *Attorney, Agent, or Firm* — Studebaker & Brackett PC

(57) ABSTRACT

A differential transformer magnetic permeability sensor includes a substrate, a drive coil, a first differential coil, a second differential coil, a first interconnection pattern, and a second interconnection pattern. The first differential coil is disposed at a side of a first surface of the substrate, and an induced voltage is generated therein when the drive coil is driven. The second differential coil is disposed at a side of a second surface of the substrate, and an induced voltage is generated therein when the drive coil is driven. The first interconnection pattern is located on the first surface and allows the first differential coil to serve as a reference coil, and the second differential coil as a sensing coil. The second interconnection pattern is located on the second surface and allows the second differential coil to serve as a reference coil, and the first differential coil as a sensing coil.

8 Claims, 12 Drawing Sheets

(51) Int. Cl.
*G01R 33/04* (2006.01)
*G01N 27/72* (2006.01)

(52) U.S. Cl.
CPC ........... *G01R 33/04* (2013.01); *G03G 15/086* (2013.01); *G03G 15/0831* (2013.01); *G03G 15/0853* (2013.01); *G03G 2215/00624* (2013.01)

(58) Field of Classification Search
USPC ............ 324/207.16, 207.17, 207.18, 207.19, 324/207.22, 228, 258
See application file for complete search history.

(56) References Cited

U.S. PATENT DOCUMENTS

2006/0132123 A1* 6/2006 Wang .................. G01N 27/902
 324/239
2008/0185666 A1* 8/2008 Yoo ..................... H01L 29/0692
 257/408
2013/0099778 A1 4/2013 Aikawa

FOREIGN PATENT DOCUMENTS

| | | |
|---|---|---|
| JP | 2001-099654 A | 4/2001 |
| JP | 2001-165910 A | 6/2001 |
| JP | 2013-101104 A | 5/2013 |

OTHER PUBLICATIONS

An Office Action; "Notice of Reasons for Rejection," issued by the Japanese Patent Office on Apr. 26, 2016, which corresponds to Japanese Patent Application No. 2014-071663 and is related to U.S. Appl. No. 14/669,543.

* cited by examiner

DIFFERENTIAL TRANSFORMER MAGNETIC PERMEABILITY SENSOR

INCORPORATION BY REFERENCE

The present application claims priority under 35 U.S.C. §119 to Japanese Patent Application No. 2014-071663, filed Mar. 31, 2014. The contents of this application are incorporated herein by reference in their entirety.

BACKGROUND

The present disclosure relates to a differential transformer magnetic permeability sensor.

A magnetic permeability sensor with the use of a differential transformer (hereinafter, referred to as "differential transformer magnetic permeability sensor") is known. The differential transformer magnetic permeability sensor is for example used for sensing the remaining toner amount or the toner concentration in an image forming apparatus in which a magnetic toner is used as a developer. Hereinafter, the differential transformer magnetic permeability sensor that senses the remaining toner amount or the toner concentration will be referred to as "toner sensor".

For example, a toner sensor that senses the toner concentration in a two-component developer includes a multi-layer substrate and planer coils. In the multi-layer substrate of the toner sensor, a first coil is disposed in a first layer, a second coil is disposed in a second layer, a third coil is disposed in a third layer, and a fourth coil is disposed in a fourth layer. For example, the first and fourth coils serve as drive coils, the second coil serves as a reference coil, and the third coil serves as a sensing coil in the toner sensor. The coils are planer coils. The above-described configuration allows the toner sensor to be compact, thin, and light-weight.

The sensor can be attached to a side of a developing device for a magnetic one-component developer. In this case, the output of the sensor changes according to the level (amount) of the magnetic toner in the developer. Thus, the sensor can be used for sensing the remaining toner amount.

SUMMARY

A differential transformer magnetic permeability sensor according to an aspect of the present disclosure includes a substrate, at least one drive coil, a first differential coil, a second differential coil, a first interconnection pattern, and a second interconnection pattern. The first differential coil is a differential coil which is disposed at a side of a first surface of the substrate and in which an induced voltage is generated when the drive coil is driven. The second differential coil is a differential coil which is disposed at a side of a second surface opposite to the first surface of the substrate and connected with the first differential coil, and in which an induced voltage is generated when the drive coil is driven. The first interconnection pattern is located on the first surface and allows the first differential coil to serve as a reference coil and the second differential coil to serve as a sensing coil. The second interconnection pattern is located on the second surface, and allows the second differential coil to serve as a reference coil and the first differential coil to serve as a sensing coil.

DETAILED DESCRIPTION

Figure 1:
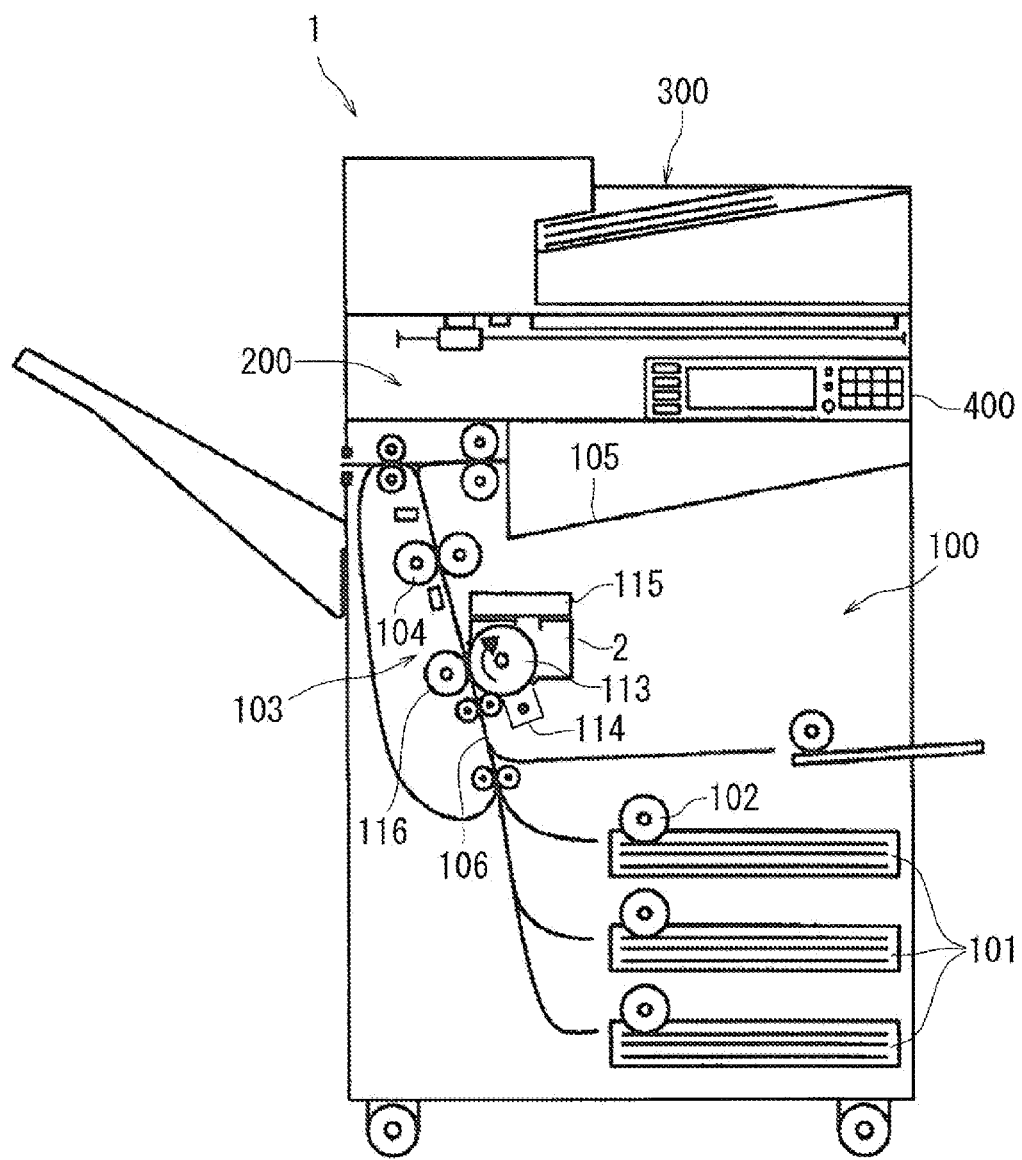
FIG. 1 is a diagram illustrating configuration of an example of an image forming apparatus including a toner sensor according to an embodiment.

An embodiment of the present disclosure will be described with reference to the accompanying drawings. The following embodiment is not intended to be limiting of the disclosure according to the appended claims. The features and the combinations of the features described in the embodiment are not entirely necessary to implement the present disclosure. In the figures of the accompanying drawings, the like reference numerals refer to similar elements.

FIG. 1 is a diagram illustrating configuration of an example of an image forming apparatus 1 including a toner sensor 3 according to the present embodiment.

The image forming apparatus 1 is for example a multi-function peripheral (MFP). The image forming apparatus 1 has functions of a scanner, a copier, a printer, and a facsimile machine (FAX). The image forming apparatus 1 includes an image forming section 100 that forms an image on paper, an image reading section 200 that reads an image on an original document, a document conveying section 300 that conveys an original document being read, and an operation panel 400 that is used when a user operates the image forming apparatus 1.

The image forming section 100 includes paper feed cassettes 101, paper feed rollers 102, an image forming unit 103, a fixing unit 104, and an exit tray 105. Each of the paper feed rollers 102 picks up paper in the corresponding paper feed cassette 101 sheet by sheet. The paper picked up by any of the paper feed rollers 102 is conveyed to the image forming unit 103 along a conveyance path 106.

The image forming unit 103 forms an image on the paper conveyed thereto from any of the paper feed cassettes 101. The image forming unit 103 includes a photosensitive drum 113, a charger 114, an exposure device 115, a transfer roller 116, and a developing device 2. The charger 114 charges the photosensitive drum 113 to a predetermined potential. The exposure device 115 outputs laser light based on image data and irradiates the photosensitive drum 113 with the laser light to form an electrostatic latent image according to the image data on the photosensitive drum 113. The image data is generated from an original document read by the image reading section 200 or transmitted from an external computer via a communication network, for example.

The developing device 2 supplies a toner onto the electrostatic latent image on the photosensitive drum 113 and develops the electrostatic latent image to form a toner image on the photosensitive drum 113. The toner sensor 3 (see FIG. 2, for example) is attached to the developing device 2. The toner sensor 3 will be described later in detail.

The transfer roller 116 transfers the toner image on the photosensitive drum 113 to the paper. The fixing unit 104 fixes the toner image to the paper. The paper on which the toner image has been fixed is conveyed along the conveyance path 106 to be ejected onto the exit tray 105.

Hereinafter, configuration of the toner sensor 3 that is attached to the developing device 2 will be described with reference to FIGS. 2-6.

Figure 2:
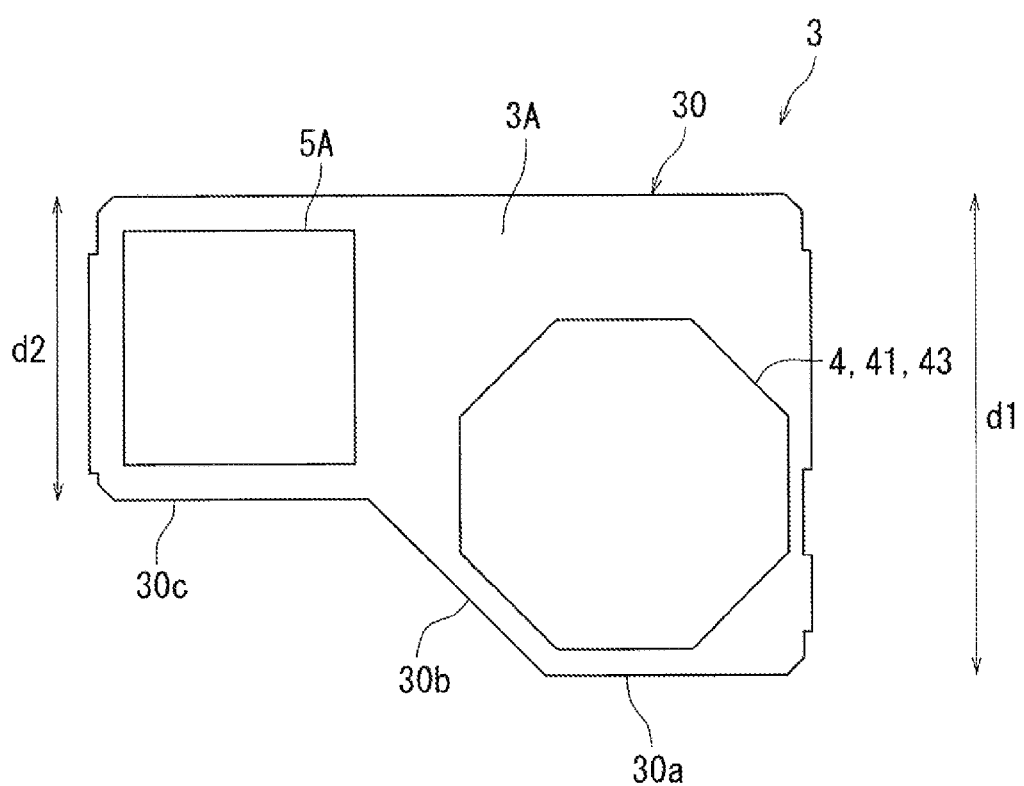
FIG. 2 is a diagram illustrating configuration of an example of a first surface of the toner sensor according to the embodiment.
Figure 3:
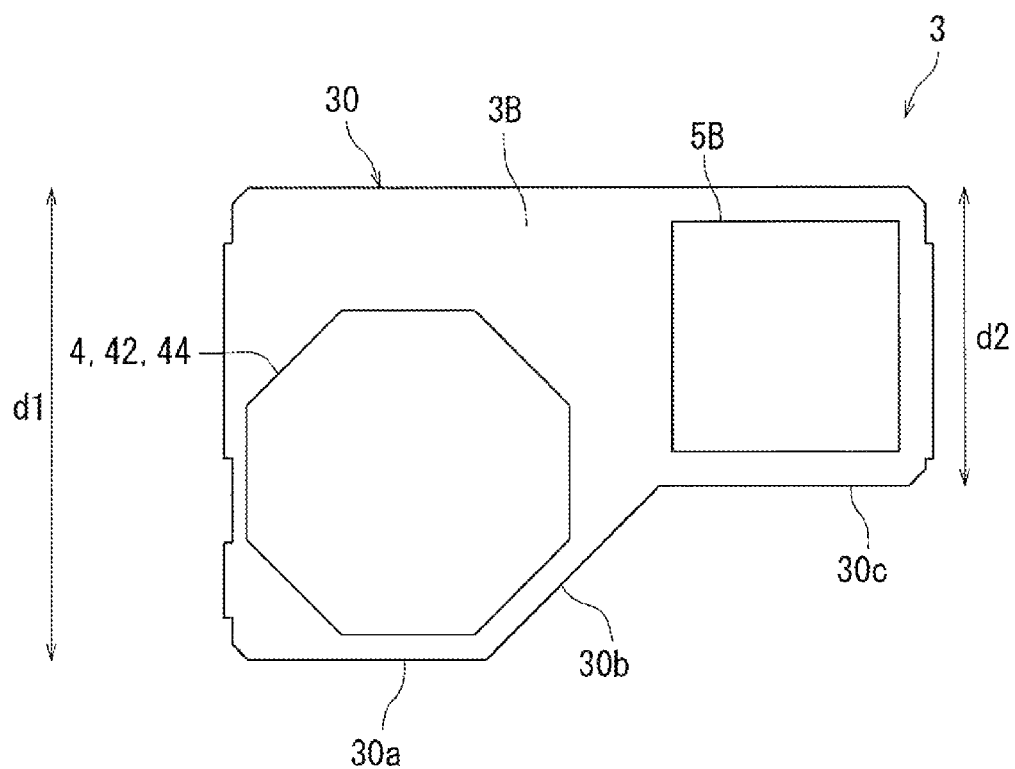
FIG. 3 is a diagram illustrating configuration of an example of a second surface of the toner sensor according to the embodiment.

FIG. 2 is a diagram illustrating configuration of an example of a first surface 3A of the toner sensor 3 according to the present embodiment. FIG. 3 is a diagram illustrating configuration of an example of a second surface 3B of the toner sensor 3 according to the present embodiment. The second surface 3B is a surface opposite to the first surface 3A.

The toner sensor 3 includes a substrate 30, planer coils 4, and interconnection patterns 5 (5A and 5B). In the present embodiment, the planer coils 4 include a first drive coil 41, a second drive coil 42, a first differential coil 43, and a second differential coil 44. A plurality of electronic components 6 are provided in either one of the interconnection patterns 5 (see FIG. 9).

The substrate 30 has a rectangular shape with a cut across one corner thereof as shown in FIGS. 2 and 3. The substrate 30 includes: a first section 30a having a first length d1 in a vertical direction, that is, a short side direction of the substrate 30; a second section 30b that is continuous from the first section 30a and has a graduated diminishing length in the vertical direction; and a third section 30c that is continuous from the second section 30b and has a second length d2 shorter than the first length d1 in the vertical direction. In the present embodiment, the planer coils 4 are disposed over the first section 30a and the second section 30b. The interconnection patterns 5 are disposed in the third section 30c. That is, the planer coils 4 are disposed near one end of the substrate 30 in a long side direction, specifically, near an end not involving the cut in the long side direction. The interconnection patterns 5 are located near the other end of the substrate 30 in the long side direction, specifically, near an end involving the cut in the long side direction. In terms of the short side direction of the substrate 30, the planer coils 4 are preferably disposed near an end involving the cut (hereinafter, referred to as "cut-involving end in the short side direction". The interconnection patterns 5 may be located over the third section 30c and the second section 30b.

As shown in FIG. 2, the first drive coil 41 and the first differential coil 43 are disposed at a side of the first surface 3A over the first section 30a and the second section 30b. The first interconnection pattern 5A is disposed on the first surface 3A in the third section 30c. The first interconnection pattern 5A allows the first differential coil 43 to serve as a reference coil and the second differential coil 44 on the second surface 3B to serve as a sensing coil. The specified electronic elements 6 provided in the first interconnection pattern 5A enable a circuit of the toner sensor 3 based on the first interconnection pattern 5A (hereinafter, referred to as "first sensor circuit"). In the first sensor circuit, the first differential coil 43 serves as a reference coil, and the second differential coil 44 serves as a sensing coil. Accordingly, in a configuration in which the electronic elements 6 are provided in the first interconnection pattern 5A on the first surface 3A, the first surface 3A having the electronic elements 6 is a reference surface. On the other hand, the second surface 3B having no electronic elements 6 is a sensing surface.

As shown in FIG. 3, the second drive coil 42 and the second differential coil 44 are disposed at a side of the second surface 3B over the first section 30a and the second section 30b. The second interconnection pattern 5B is disposed on the second surface 3B in the third section 30c. The second interconnection pattern 5B allows the second differential coil 44 to serve as a reference coil and the first differential coil 43 to serve as a sensing coil. The specified electronic elements 6 provided in the second interconnection pattern 5B enable a circuit of the toner sensor 3 based on the second interconnection pattern 5B (hereinafter, referred to as "second sensor circuit"). In the second sensor circuit, the second differential coil 44 serves as a reference coil, and the first differential coil 43 serves as a sensing coil. Accordingly, in a configuration in which the electronic elements 6 are provided in the second interconnection pattern 5B on the second surface 3B, the second surface 3B having the electronic elements 6 is a reference surface. On the other hand, the first surface 3A having no electronic elements 6 is a sensing surface.

Either the first surface 3A or the second surface 3B can be used as a sensing surface by selecting either the interconnection pattern 5A or the interconnection pattern 5B in the toner sensor 3 according to the present embodiment. That is, both the first surface 3A and the second surface 3B can be used as a reference surface or a sensing surface in the toner sensor 3 according to the present embodiment. As shown in FIGS. 2 and 3, the shape of the substrate 30 in a view from the side of the first surface 3A and the shape of the substrate 30 in a view from the side of the second surface 3B are different. The positional relationship between the planer coils 4 and the third section 30c is also different in the substrate 30 seen from the side of the first surface 3A than in the substrate 30 seen from the side of the second surface 3B. When the toner sensor 3 is to be attached to a developing device in such a manner that the second surface 3B serves as a sensing surface, for example, the third section 30c may obstruct the planer coils 4 from being in an appropriate position and an appropriate orientation. In this case, the toner sensor 3 can be attached to the developing device in such a manner that the first surface 3A serves as a sensing surface to change the position of the third section 30c relative to the planer coils 4, and thus the planer coils 4 can be in the appropriate position and orientation.

Figure 4:
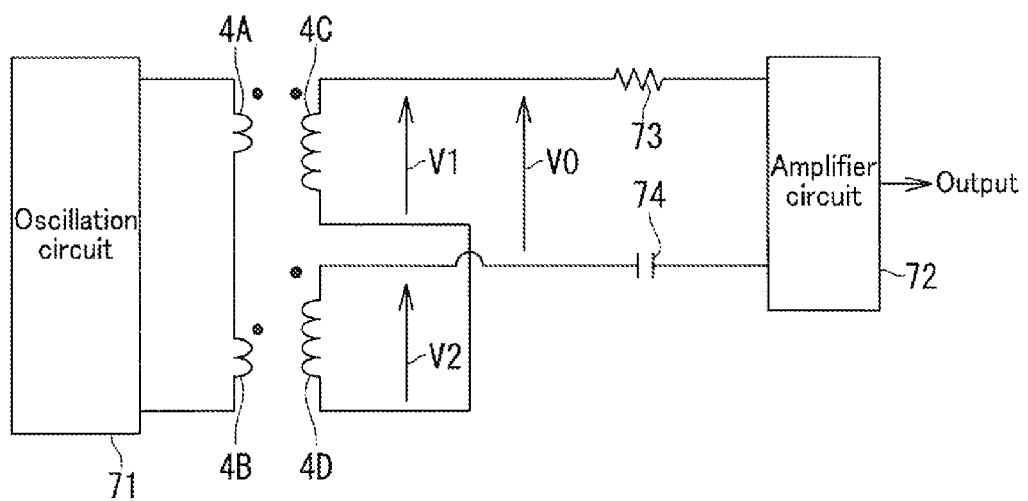
FIG. 4 is a circuit diagram illustrating an example of the toner sensor according to the embodiment.

FIG. 4 is a circuit diagram illustrating an example of the toner sensor 3 according to the present embodiment.

Both the first sensor circuit and the second sensor circuit have a circuit configuration illustrated in FIG. 4. Specifically, the sensor circuit (the first sensor circuit or the second sensor circuit) includes four coils (a first coil 4A, a second coil 4B, a third coil 4C, and a fourth coil 4D), an oscillation circuit 71, an amplifier circuit 72, a resistor 73, and a capacitor 74. The first coil 4A and the second coil 4B are drive coils. The third coil 4C is a reference coil. The fourth coil 4D is a sensing coil.

The four coils (the first coil 4A, the second coil 4B, the third coil 4C, and the fourth coil 4D) shown in the circuit diagram correspond to the four planer coils 4 (the first drive coil 41, the second drive coil 42, the first differential coil 43, and the second differential coil 44) in the toner sensor 3. Assuming FIG. 4 is representing the circuit configuration of the first sensor circuit, the first coil 4A corresponds to the first drive coil 41, the second coil 4B corresponds to the second drive coil 42, the third coil 4C corresponds to the first differential coil 43, and the fourth coil 4D corresponds to the second differential coil 44. Assuming FIG. 4 is representing the circuit configuration of the second sensor circuit, on the other hand, the first coil 4A corresponds to the second drive coil 42, the second coil 4B corresponds to the first drive coil 41, the third coil 4C corresponds to the second differential coil 44, and the fourth coil 4D corresponds to the first differential coil 43.

The oscillation circuit 71 generates a high-frequency drive current that drives the first coil 4A and the second coil 4B. The first coil 4A and the second coil 4B are connected in series. Specifically, one end of the first coil 4A and one end of the second coil 4B are connected so that the magnetic flux generated through the first coil 4A and the magnetic flux generated through the second coil 4B are in the same direction when the drive current flows through the first coil 4A and the second coil 4B. The other end of the first coil 4A and the other end of the second coil 4B are connected to the oscillation circuit 71.

The third coil 4C is magnetically coupled to the first coil 4A. The fourth coil 4D is magnetically coupled to the second coil 4B. One end of the third coil 4C and one end of the fourth coil 4D are differentially connected in series. Specifically, one end of the third coil 4C and one end of the fourth coil 4D are connected so that the magnetic flux generated through the third coil 4C and the magnetic flux generated through the fourth coil 4D are in opposite directions when the drive current flows through the third coil 4C and the fourth coil 4D. Thus, a differential voltage V0 is input to the amplifier circuit 72. The differential voltage V0 is a voltage calculated by subtracting an induced voltage V2 in the fourth coil 4D from an induced voltage V1 in the third coil 4C.

The other end of the third coil 4C is connected to the amplifier circuit 72 via the resistor 73. The resistor 73 is connected to a base of a bipolar transistor in the amplifier circuit 72 to be used for setting the amplification factor of the amplifier circuit 72. The other end of the fourth coil 4D is connected to the amplifier circuit 72 via the capacitor 74. The capacitor 74 has a function of removing a DC component of the differential voltage V0. Thus, an AC component of the differential voltage V0 is input to the amplifier circuit 72.

Once the drive current generated in the oscillation circuit 71 flows through the first coil 4A and the second coil 4B, the induced voltage V1 is generated in the third coil 4C, and the induced voltage V2 is generated in the fourth coil 4D. When a toner is present near the fourth coil 4D, the induced voltage V2 is greater than the induced voltage V1, and therefore the differential voltage V0 is not 0 V. The differential voltage V0 is amplified in the amplifier circuit 72, and a signal is output from the amplifier circuit 72. The remaining toner amount is sensed using the signal.

The toner sensor 3 may further include a selection section that zeroes the differential transformer. The selection section is disposed in a part of the first section 30a where the planer coil 4 is not present, for example. The selection section functions to adjust the value of the induced voltage V2 when no toner is present to a value equal to or greater than the induced voltage V1 for both the first sensor circuit and the second sensor circuit. Thus, the first sensor circuit and the second sensor circuit are enabled to provide an output that increases with increase in the remaining toner amount.

Figure 5:
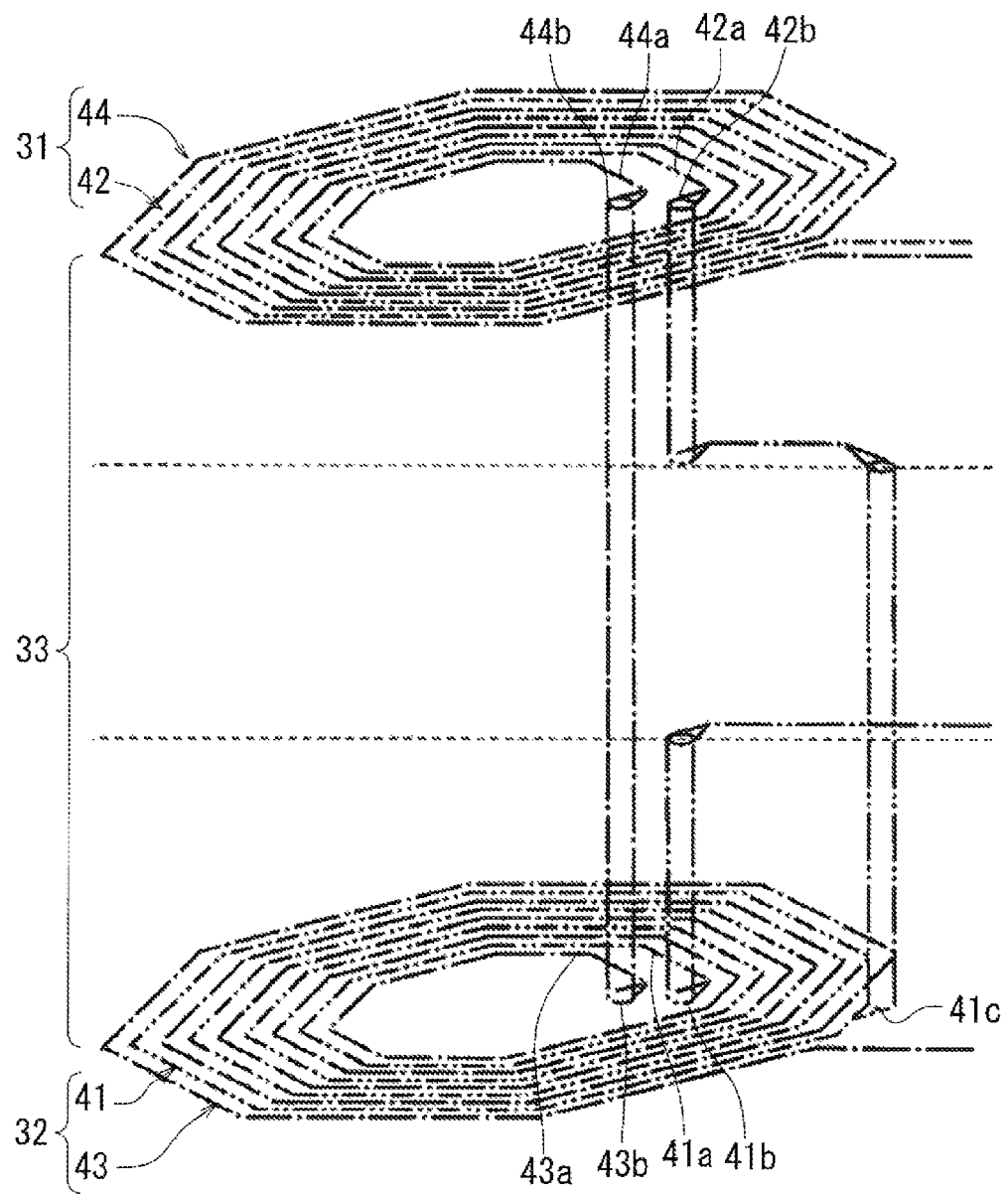
FIG. 5 is a diagram illustrating configuration of an example of a planer coil disposed in the toner sensor according to the embodiment.
Figure 6:
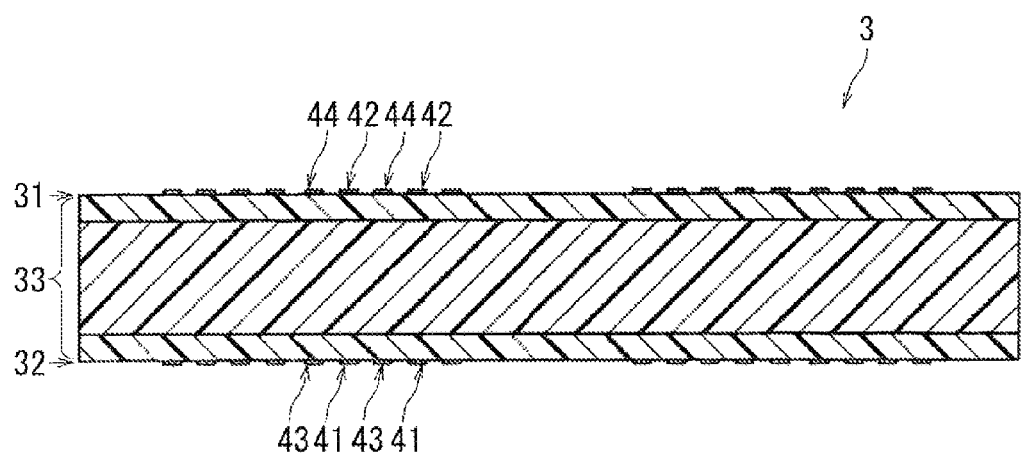
FIG. 6 is a cross sectional view of a part of the toner sensor according to the embodiment where the coil is disposed.

FIG. 5 is a diagram illustrating configuration of an example of the planer coils 4 disposed in the toner sensor 3 according to the present embodiment. FIG. 6 is a cross sectional view of a part of the toner sensor 3 according to the present embodiment where the coils are disposed. In the present embodiment, the part where the coils are disposed is the first section 30a and the second section 30b of the substrate 30.

As shown in FIGS. 5 and 6, the substrate 30 has a multi-layer structure including a first coil layer 31 at the side of the second surface 3B, a second coil layer 32 at the side of the first surface 3A, and an insulating layer 33. The insulating layer 33 is disposed between the first coil layer 31 and the second coil layer 32.

The second drive coil 42 and the second differential coil 44 are disposed in the first coil layer 31. In the present embodiment, the second drive coil 42 is formed from a wire 42a wound into an octagonal shape. The second differential coil 44 is formed from a wire 44a wound into an octagonal shape. The wire 42a forming the second drive coil 42 and the wire 44a forming the second differential coil 44 are wound in parallel in the same direction.

The first drive coil 41 and the first differential coil 43 are disposed in the second coil layer 32. In the present embodiment, the first drive coil 41 is formed from a wire 41a wound into an octagonal shape. The first differential coil 43 is formed from a wire 43a wound into an octagonal shape. The wire 41a forming the first drive coil 41 and the wire 43a forming the first differential coil 43 are wound in parallel in the same direction.

As shown in FIG. 5, the first drive coil 41 and the second drive coil 42 are electrically connected so that the flow of the drive current through the first drive coil 41 and the flow of the drive current through the second drive coil 42 are in the same direction. The first differential coil 43 and the second differential coil 44 are electrically connected so that the flow of the induced current in the first differential coil 43 and the flow of the induced current in the second differential coil 44 are in opposite directions.

Hereinafter, different shapes of two developing devices 2 (a first developing device 2A and a second developing device 2B) and manners of attachment of the toner sensor 3 thereto will be described with reference to FIGS. 7-10.

Figure 7:
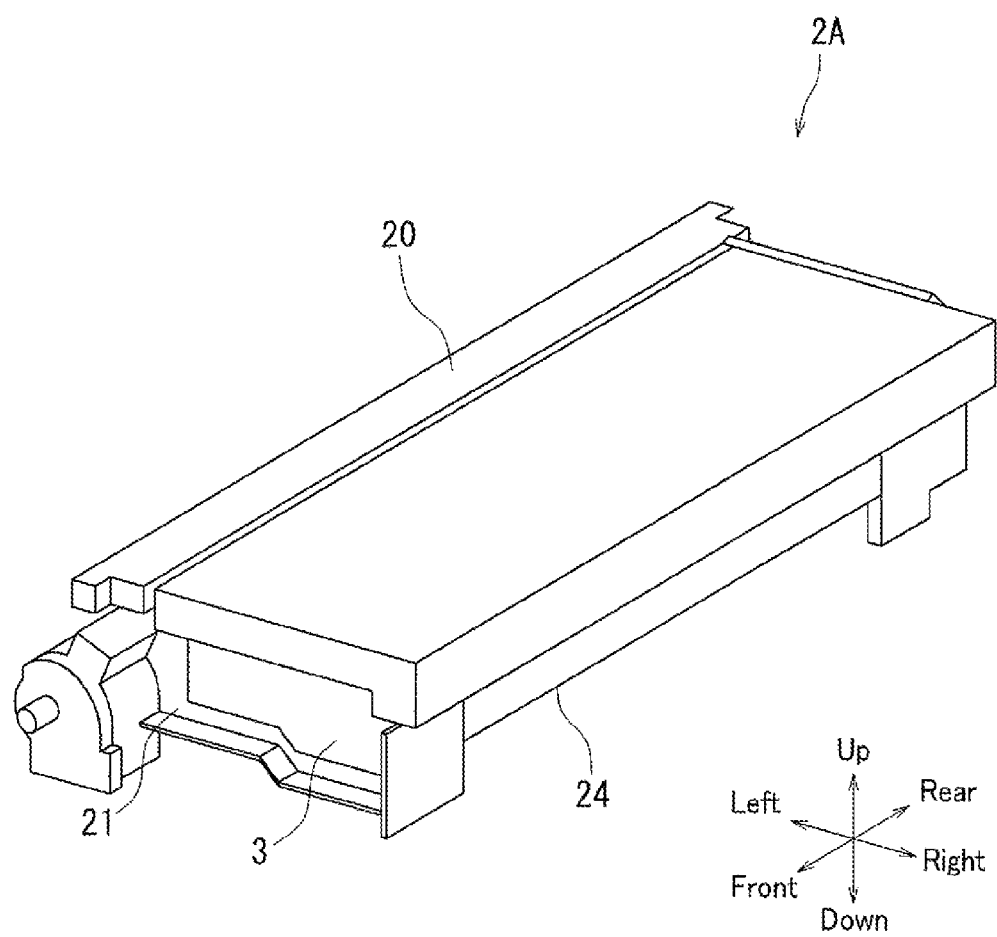
FIG. 7 is a first perspective view of a first developing device.
Figure 8:
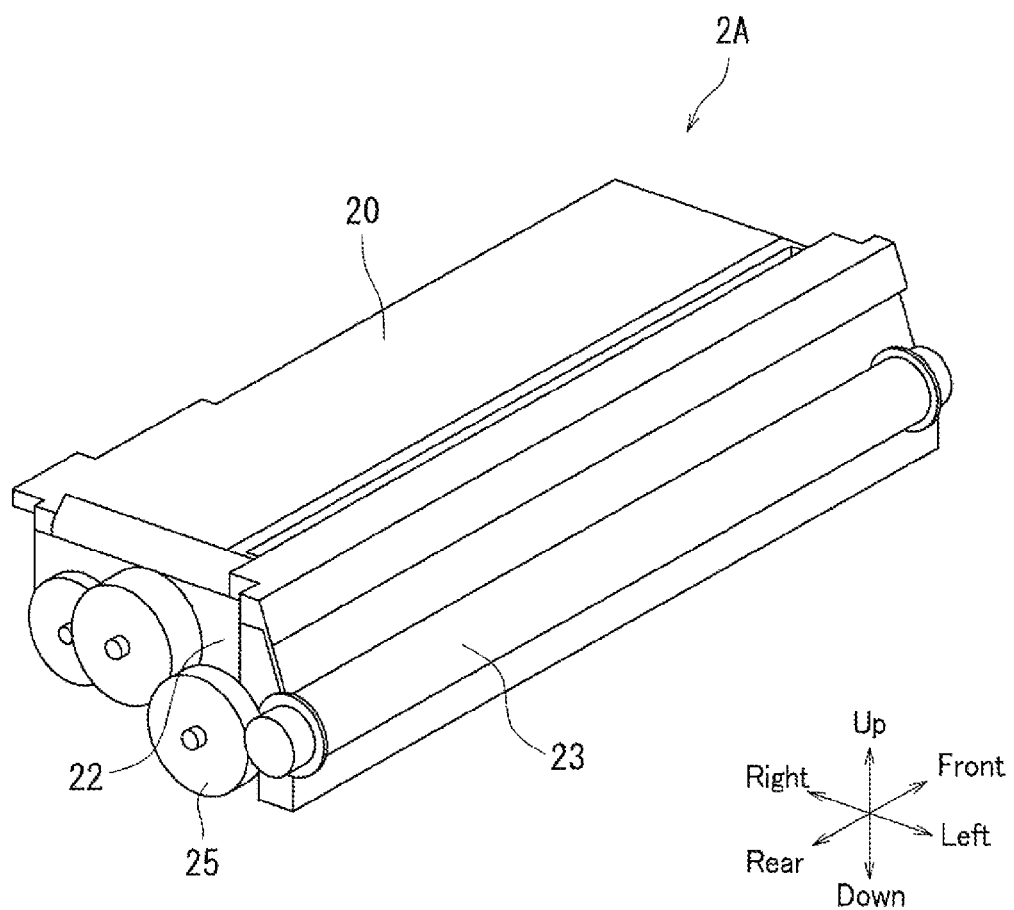
FIG. 8 is a second perspective view of a first developing device.
Figure 9:
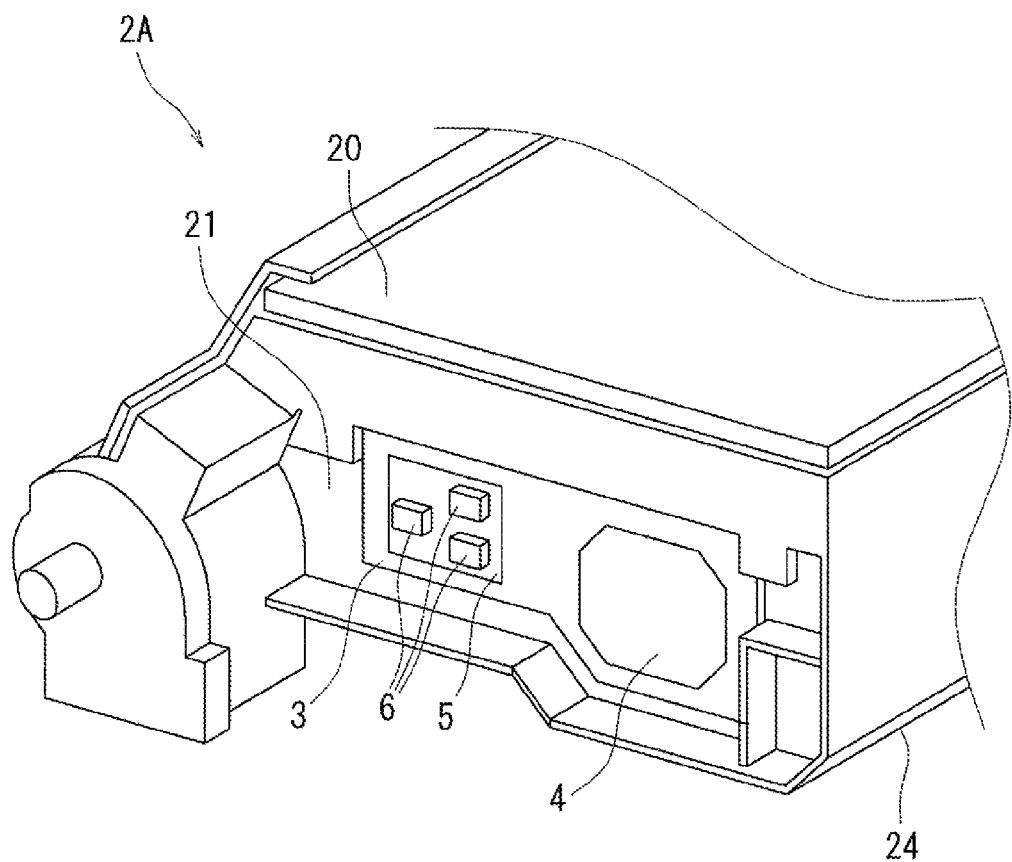
FIG. 9 is an enlarged view of a side of the first developing device where a sensor is attached.

FIG. 7 is a first perspective view of the first developing device 2A. FIG. 8 is a second perspective view of the first developing device 2A. FIG. 9 is an enlarged view of a side of the first developing device 2A where the sensor is attached. The first perspective view is a top front view of the first developing device 2A. The second perspective view is a top rear view of the first developing device 2A. The shape of the first developing device 2A and the manner of the attachment of the toner sensor 3 to the first developing device 2A will be described with reference to FIGS. 7-9.

The first developing device 2A has a shape elongated in front and rear directions. The first developing device 2A includes a front wall 21 and a rear wall 22 at opposite ends in the front and rear directions. The front wall 21 and the rear wall 22 are parts of a housing 20 of the first developing device 2A.

A developing roller 23 is disposed at a left side of the first developing device 2A. A toner containing section 24 that contains a toner is disposed at a right side of the first developing device 2A. A drive mechanism 25 that drives the developing roller 23, a stirring roller within the housing 20, and the like is disposed in the rear wall 22 of the first developing device 2A.

The front wall 21 of the first developing device 2A has a rectangular shape with a cut across a corner, specifically, across a lower left corner when seen from the front. That is, the right side, which is the side where the toner containing section 24 is disposed, of the front wall 21 has a length in upward and downward directions longer than the left side, which is the side where the developing roller 23 is disposed, of the front wall 21.

In order to dispose the sensing coil in an appropriate position and an appropriate orientation, the toner sensor 3 is attached to the first developing device 2A having the above-described configuration as follows. That is, the toner sensor 3 is attached to the front wall 21 of the first developing device 2A in such a manner that: the second surface 3B serves as a sensing surface; the first section 30a is disposed at the right side of the first developing device 2A, that is, at the side where the toner containing section 24 is disposed; the cut-involving end in the short side direction is at the bottom; and the sensing surface faces the first developing device 2A. Thus, the sensing coil is disposed close to the toner containing section 24 and in the lowest possible position to be capable of high-accuracy sensing.

Figure 10:
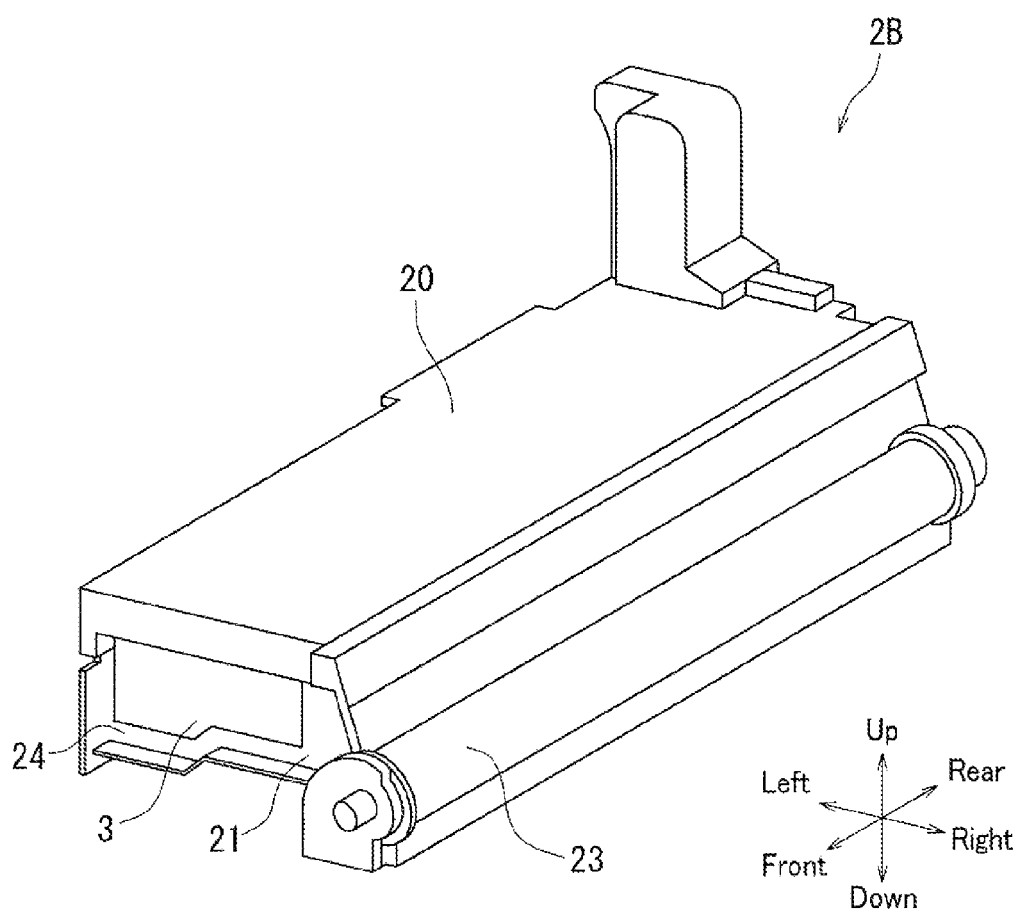
FIG. 10 is a perspective view of a second developing device.

FIG. 10 is a perspective view of the second developing device 2B. The perspective view as FIG. 10 is a top front view of the second developing device 2B. The shape of the second developing device 2B and the manner of the attachment of the toner sensor 3 to the second developing device 2B will be described with reference to FIG. 10.

As in the case of the first developing device 2A, the second developing device 2B has a shape elongated in the front and rear directions, and includes the front wall 21 and the rear wall 22 at opposite ends in the front and rear directions.

The developing roller 23 is disposed at the right side of the second developing device 2B, and the toner containing section 24 is disposed at the left side of the second developing device 2B. That is, the positions of the developing roller 23 and the toner containing section 24 in the case of the second developing device 2B are opposite to the positions of the developing roller 23 and the toner containing section 24 in the case of the first developing device 2A. As in the case of the first developing device 2A, the drive mechanism 25, not shown in FIG. 10, that drives the developing roller 23, the magnetic roller, and the like is disposed in the rear wall 22 of the second developing device 2B.

The front wall 21 of the second developing device 2B has a rectangular shape with a cut across a corner, specifically, across a lower right corner when seen from the front. That is, the left side, which is the side where the toner containing section 24 is disposed, of the front wall 21 has a length in the upward and downward directions longer than the right side, which is the side where the developing roller 23 is disposed, of the front wall 21. As described above, the shape of the front wall 21 of the second developing device 2B is different from the shape of the front wall 21 of the first developing device 2A. Accordingly, if the toner sensor 3 is attached to the second developing device 2B in the same manner as in the attachment to the first developing device 2A such that the second surface 3B serves as a sensing surface, the third section 30c obstructs the sensing coil from being in an appropriate position and an appropriate orientation.

In order to dispose the sensing coil in an appropriate position and an appropriate orientation, therefore, the toner sensor 3 is attached to the second developing device 2B having the above-described configuration as follows. That is, the toner sensor 3 is attached to the front wall 21 of the second developing device 2B in such a manner that: the first surface 3A serves as a sensing surface; the first section 30a is disposed at the left side of the second developing device 2B, that is, at the side where the toner containing section 24 is disposed; the cut-involving end in the short side direction is at the bottom; and the sensing surface faces the second developing device 2B. Thus, the sensing coil is disposed close to the toner containing section 24 and in the lowest possible position to be capable of high-accuracy sensing.

Figure 11:
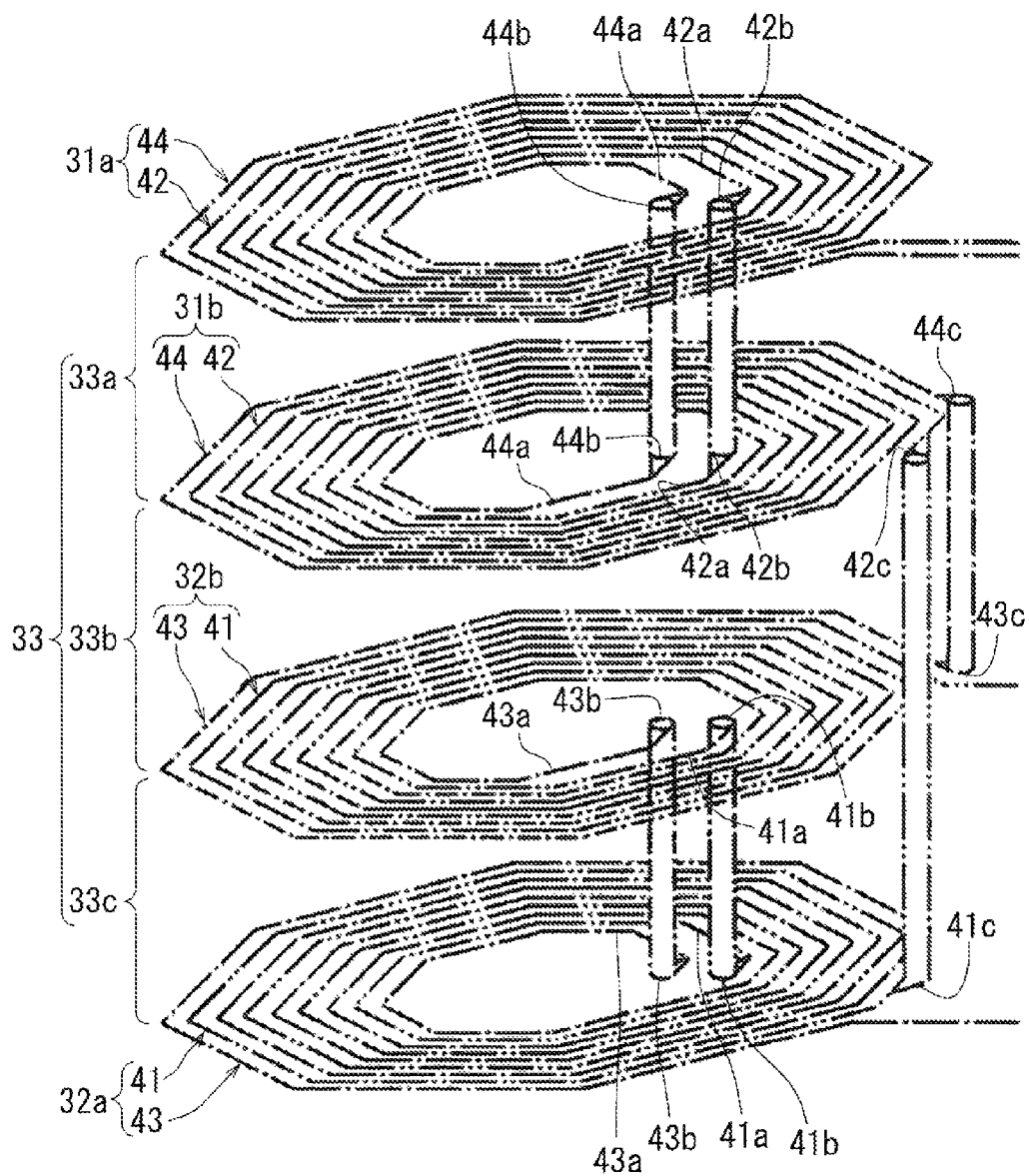
FIG. 11 is a diagram illustrating configuration of a planer coil disposed in a toner sensor according to a variation.
Figure 12:
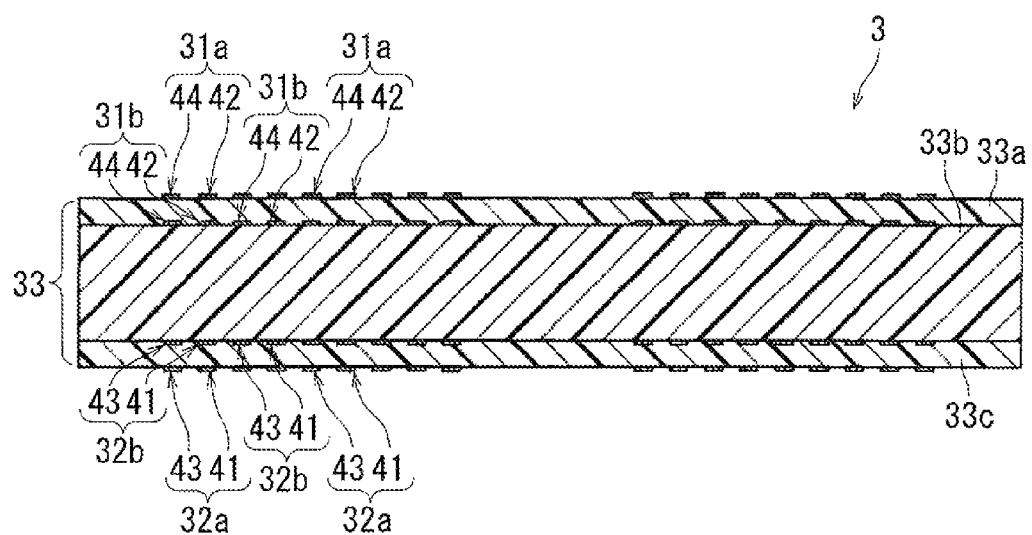
FIG. 12 is a cross sectional view of a part of the toner sensor according to the variation where the coil is disposed.

FIG. 11 is a diagram illustrating configuration of the planer coils 4 disposed in the toner sensor 3 according to a variation. FIG. 12 is a cross sectional view of a part of the toner sensor 3 according to the variation where the coils are disposed. The configuration of the planer coils 4 disposed in the toner sensor 3 according to the variation will be described with reference to FIGS. 11 and 12.

In the variation, the substrate 30 includes two first coil layers 31 (a first coil layer 31a and a first coil layer 31b), two second coil layers 32 (a second coil layer 32a and a second coil layer 32b), and three insulating layers 33 (an upper insulating layer 33a, a middle insulating layer 33b, and a lower insulating layer 33c).

The first coil layer 31a has substantially the same configuration as the first coil layer 31 shown in FIG. 5. The second coil layer 32a has substantially the same configuration as the second coil layer 32 shown in FIG. 5.

The first coil layer 31b is formed between the upper insulating layer 33a and the middle insulating layer 33b. As in the case of the first coil layer 31a, the second drive coil 42 and the second differential coil 44 are disposed in the first coil layer 31b. The second drive coil 42 and the second differential coil 44 are formed from the wire 42a and the wire 44a, respectively, each wound into an octagonal shape. The wire 42a forming the second drive coil 42 and the wire 44a forming the second differential coil 44 are wound in parallel in the same direction. In the variation, the direction of winding the wires 42a and 44a is different in the first coil layer 31a than in the first coil layer 31b.

The second coil layer 32b is formed between the lower insulating layer 33c and the middle insulating layer 33b. As in the case of the second coil layer 32a, the first drive coil 41 and the first differential coil 43 are disposed in the second coil layer 32b. The first drive coil 41 and the first differential coil 43 are formed from the wire 41a and the wire 43a, respectively, each wound into an octagonal shape. The wire 41a forming the first drive coil 41 and the wire 43a forming the first differential coil 43 are wound in parallel in the same direction. In the variation, the direction of winding the wires 41a and 43a is different in the second coil layer 32a than in the second coil layer 32b.

As described above, the structure of the planer coils 4 disposed on the substrate 30 is not limited to the two-layer structure having the two coil layers 31 and 32 as shown in FIG. 6 but may be the four-layer structure having the four coil layers 31a, 31b, 32a, and 32b as shown in FIG. 11. Alternatively, a multi-layer structure having five or more coil layers may be employed.

The present embodiment provides the toner sensor 3 in which both the first surface 3A and the second surface 3B can be used as a reference surface or a sensing surface. Which of the first surface 3A and the second surface 3B should serve as a sensing surface for attaching the toner sensor 3 to the developing device 2 can be selected according to the shape of a part of the developing device 2 where the toner sensor 3 is attached. Thus, the toner sensor 3 can be attached to developing devices in various shapes in such a manner that the sensing coil is disposed in an appropriate position and an appropriate orientation.

So far, one embodiment of the present disclosure has been described. However, the present disclosure is not limited to the embodiment, and various alterations can be made within the scope not departing from the gist of the present disclosure.

For example, one coil layer may include one planer coil 4, although one coil layer includes two planer coils 4 according to the embodiment. In the case of a four-layer structure having the four coil layers 31a, 31b, 32a, and 32b, for example, the coil layer 31a may include the second differential coil 44, the coil layer 31b may include the second drive coil 42, the coil layer 32b may include the first drive coil 41, and the coil layer 32a may include the first differential coil 43.

The differential transformer magnetic permeability sensor is not limited to the toner sensor 3 and may be a sensor for sensing the amount, the mixing ratio, or the like of any substances other than toner, although the toner sensor 3 has been described as an example of the differential transformer magnetic permeability sensor in the embodiment.

What is claimed is:

1. A differential transformer magnetic permeability sensor comprising:
   a substrate;
   at least one drive coil;
   a first differential coil which is disposed at a side of a first surface of the substrate and in which an induced voltage is generated when the at least one drive coil is driven;
   a second differential coil which is disposed at a side of a second surface opposite to the first surface of the substrate and connected with the first differential coil, and in which an induced voltage is generated when the at least one drive coil is driven;
   a first interconnection pattern that is located on the first surface and allows the first differential coil to serve as a reference coil and the second differential coil to serve as a sensing coil; and
   a second interconnection pattern that is located on the second surface and allows the second differential coil to serve as a reference coil and the first differential coil to serve as a sensing coil, wherein
   the substrate has:
      a coil region in which the at least one drive coil, the first differential coil, and the second differential coil are disposed; and
      an interconnection pattern region that is different from the coil region and in which the first interconnection pattern and the second interconnection pattern are disposed.

2. The differential transformer magnetic permeability sensor according to claim 1, wherein
   a specified electronic component is provided in the first interconnection pattern but is not provided in the second interconnection pattern to enable a circuit based on the first interconnection pattern in which the first differential coil serves as a reference coil and the second differential coil serves as a sensing coil, and
   the specified electronic component is provided in the second interconnection pattern but is not provided in the first interconnection pattern to enable a circuit based on the second interconnection pattern in which the second differential coil serves as a reference coil and the first differential coil serves as a sensing coil.

3. The differential transformer magnetic permeability sensor according to claim 1, wherein
   the first differential coil and the second differential coil are disposed near one end of the substrate in terms of a long side direction of the substrate,
   the first interconnection pattern and the second interconnection pattern are disposed near another end of the substrate in terms of the long side direction, and
   a shape of the substrate at the one end is different than a shape of the substrate at the other end.

4. The differential transformer magnetic permeability sensor according to claim 3, wherein
   the substrate has a general rectangular shape with a cut across one corner thereof, and
   a length of the substrate in terms of a short side direction of the substrate at the one end is longer than a length of the substrate in terms of the short side direction at the other end.

5. The differential transformer magnetic permeability sensor according to claim 1, wherein
   the at least one drive coil includes a first drive coil disposed at the side of the first surface and a second drive coil disposed at the side of the second surface and connected with the first drive coil,
   the induced voltage is generated in the first differential coil when the first drive coil is driven, and
   the induced voltage is generated in the second differential coil when the second drive coil is driven.

6. The differential transformer magnetic permeability sensor according to claim 5, wherein
   the substrate has a multi-layer structure,
   the first drive coil and the first differential coil are disposed in one or more layers of the multi-layer structure that are located at the side of the first surface of the substrate, and
   the second drive coil and the second differential coil are disposed in one or more layers of the multi-layer structure that are located at the side of the second surface of the substrate.

7. The differential transformer magnetic permeability sensor according to claim 6, wherein
   the first drive coil and the first differential coil are disposed in the same layer among the one or more layers that are located at the side of the first surface of the substrate, and
   the second drive coil and the second differential coil are disposed in the same layer among the one or more layers that are located at the side of the second surface of the substrate.

8. The differential transformer magnetic permeability sensor according to claim 6, wherein
   the first drive coil and the first differential coil are disposed in different layers among the one or more layers that are located at the side of the first surface of the substrate, and
   the second drive coil and the second differential coil are disposed in different layers among the one or more layers that are located at the side of the second surface of the substrate.

* * * * *